United States Patent
Grueebler et al.

(10) Patent No.: US 11,752,036 B2
(45) Date of Patent: Sep. 12, 2023

(54) MEMBRANE DELAMINATION DEVICE

(71) Applicant: Alcon Inc., Fribourg (CH)

(72) Inventors: Reto Grueebler, Greifensee (CH);
Thomas Linsi, Schaffhausen (CH);
Niccolo Maschio, Winterthur (CH)

(73) Assignee: Alcon Inc., Fribourg (CH)

( * ) Notice: Subject to any disclaimer, the term of this patent is extended or adjusted under 35 U.S.C. 154(b) by 406 days.

(21) Appl. No.: 17/065,654

(22) Filed: Oct. 8, 2020

(65) Prior Publication Data
US 2021/0113376 A1    Apr. 22, 2021

Related U.S. Application Data
(60) Provisional application No. 62/915,726, filed on Oct. 16, 2019.

(51) Int. Cl.
| | | |
|---|---|---|
| *A61F 9/007* | (2006.01) | |
| *B26B 29/02* | (2006.01) | |
| *A61F 9/013* | (2006.01) | |

(52) U.S. Cl.
CPC ........ *A61F 9/00754* (2013.01); *A61F 9/0133* (2013.01); *B26B 29/02* (2013.01)

(58) Field of Classification Search
CPC .. A61F 9/007; A61F 9/00709; A61F 9/00736; A61F 9/00754; A61F 9/00763; A61F 9/013; A61F 9/0133; A61B 17/3211; A61B 2017/320008; A61B 2017/32113; B26B 29/02
See application file for complete search history.

(56) References Cited

U.S. PATENT DOCUMENTS

| | | | |
|---|---|---|---|
| 5,904,699 A | * | 5/1999 | Schwemberger .. A61B 17/3496 604/164.08 |
| 9,827,141 B2 | | 11/2017 | Schaller |
| 10,675,180 B2 | | 6/2020 | Grueebler |
| 10,864,001 B2 | | 12/2020 | Vezzu |
| 2008/0319463 A1 | | 12/2008 | Hickingbotham |
| 2015/0238355 A1 | | 8/2015 | Vezzu |
| 2017/0360603 A1 | | 12/2017 | Grueebler |
| 2020/0246034 A1 | | 8/2020 | Linsi |
| 2020/0375797 A1 | | 12/2020 | Maschio |
| 2020/0375844 A1 | | 12/2020 | Maschio |

OTHER PUBLICATIONS

Alcon Global Vitreoretinal Product Catalog, dated Feb. 2014, pp. 1 and 25-48.

* cited by examiner

*Primary Examiner* — Robert A Lynch
(74) *Attorney, Agent, or Firm* — PATTERSON & SHERIDAN, LLP

(57) ABSTRACT

Particular embodiments disclosed herein provide a membrane delamination device for delaminating a membrane from a retina of an eye. The membrane delamination device comprises a blade, a first lever coupled to the blade, and a second lever coupled to the blade. The first lever and the second lever are at least partially housed by a first shaft of a hand-piece. The first lever is fixedly coupled to the first shaft. The second lever is fixedly coupled to the hand-piece. The blade at least partially extends beyond a distal end of the first shaft. The membrane delamination device is configured to be actuated as a result of longitudinal movement of the second lever within and in relation to the first shaft. The second lever moves longitudinally within and in relation to the first shaft due to an application of force to the second lever through the hand-piece.

20 Claims, 5 Drawing Sheets

MEMBRANE DELAMINATION DEVICE

PRIORITY CLAIM

This application claims the benefit of priority of U.S. Provisional Patent Application Ser. No. 62/915,726 titled "MEMBRANE DELAMINATION DEVICE," filed on Oct. 16, 2019, whose inventors are Reto Grueebler, Thomas Linsi and Niccolo Maschio, which is hereby incorporated by reference in its entirety as though fully and completely set forth herein.

TECHNICAL FIELD

The present disclosure relates generally to a membrane delamination device ("device") for ophthalmic surgery.

BACKGROUND

Membrane removal is a useful surgical treatment for different retinal surface diseases. A membrane generally refers to a very thin layer of scar tissue that forms on the surface of the retina. Different types of membranes include epi-retinal membranes (ERM) and proliferative membranes. Each of these membranes may develop as a result of a different eye disease or condition. For example, in the case of ERMs, the scar tissue formation can be associated with a number of ocular conditions, such as prior retinal tears or detachments, or retinal vascular diseases, such as diabetic retinopathy or venous occlusive diseases. ERMs can also be developed due to trauma associated with ocular surgery or be associated with intraocular (inside the eye) inflammation. In another example, proliferative membranes may be caused by diabetic retinopathy, which in its advanced form causes new abnormal blood vessels to proliferate (increase in number) on the surface of the retina, thereby forming a proliferative membrane.

Surgical techniques for the removal or peeling of membranes require skill and patience. Precise and carefully constructed surgical instruments are used for each segment of the surgical technique. The surgical treatment itself includes grasping an edge of the membrane, and peeling the membrane. However, peeling certain membranes may pose additional complexities because the membranes may have developed tissues or vessels (referred to herein as "connective tissues") that attach the membranes to the retina. Accordingly, in such cases, the surgeon has to delaminate or remove the connective tissues between the membrane and the retina in order to continue to peel the membrane. Currently, a surgeon may use forceps to hold the membrane and scissors to delaminate the connective tissue. The delaminated membrane is then removed with the forceps. A surgeon may also only use forceps to delaminate the membrane. However, utilizing devices such as forceps or scissors may damage the surface of the retina.

BRIEF SUMMARY

The present disclosure relates generally to a membrane delamination device for ophthalmic surgery.

Particular embodiments disclosed herein provide a membrane delamination device for delaminating a membrane from a retina of an eye. The delamination device comprises a blade, a first lever coupled to the blade, and a second lever coupled to the blade. The first lever and the second lever are at least partially housed by a first shaft of a hand-piece. The first lever is fixedly coupled to the first shaft. The second lever is fixedly coupled to the hand-piece. The blade at least partially extends beyond a distal end of the first shaft. The membrane delamination device is configured to be actuated as a result of longitudinal movement of the second lever within and in relation to the first shaft. The second lever moves longitudinally within and in relation to the first shaft due to an application of force to the second lever through the hand-piece. The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a membrane delamination device for ophthalmic surgery.

Figure 1:
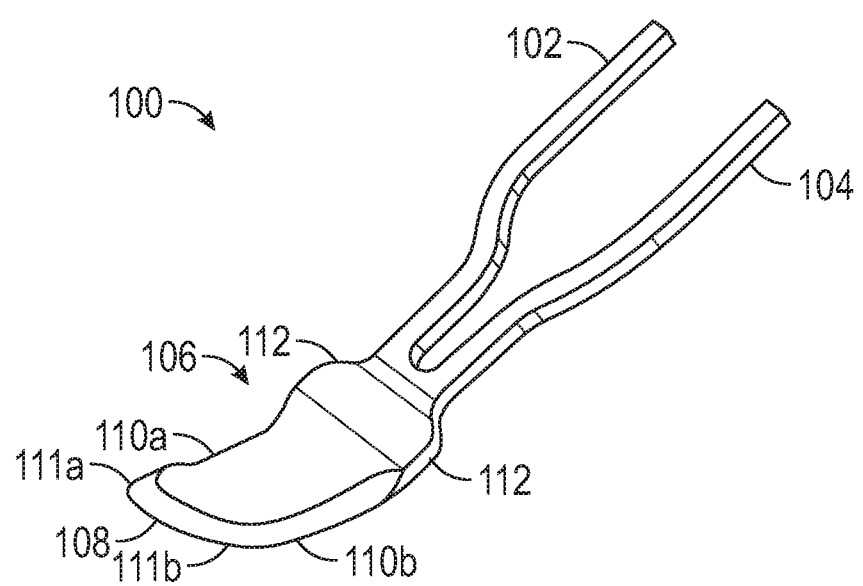
FIG. 1 illustrates an example device, in accordance with certain embodiments of the present disclosure.

FIG. 1 illustrates a device 100. In certain embodiments, device 100 is configured to be used in conjunction with a hand-piece (not shown) that is able to actuate device 100, such as for cutting connective tissues between a membrane and the surface of the retina. Device 100 includes a blade 106, a first lever 102 and a second lever 104. Blade 106 comprises a sharp tip 108 (referred to as "tip 108"), sharp sides 110a-110b (referred to individually as "side 110a" and "side 110b," or collectively as "sides 110"), sharp corners 111a-111b (referred to individually as "corner 111a" and "corner 111b," or collectively referred to as "corners 111"), and non-sharp or flat sides 112. In certain embodiments, tip 108, sides 110, and corners 111 are configured to sever or cut any connective tissue that they come in contact with.

Figure 2A:
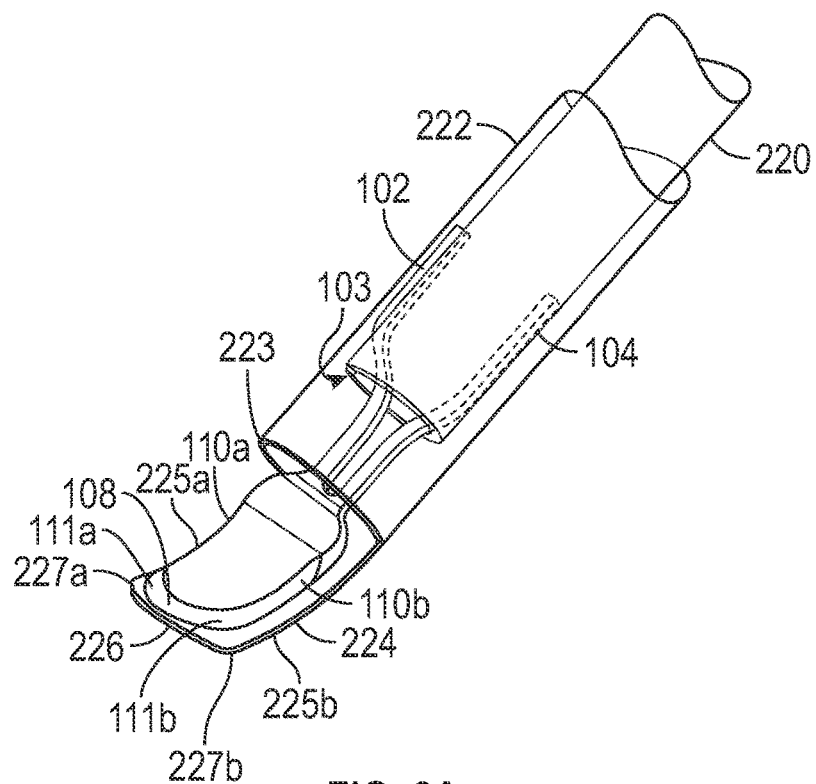
FIG. 2A illustrates a device partially positioned within a shaft of a hand-piece, in accordance with certain embodiments of the present disclosure.
Figure 2B:
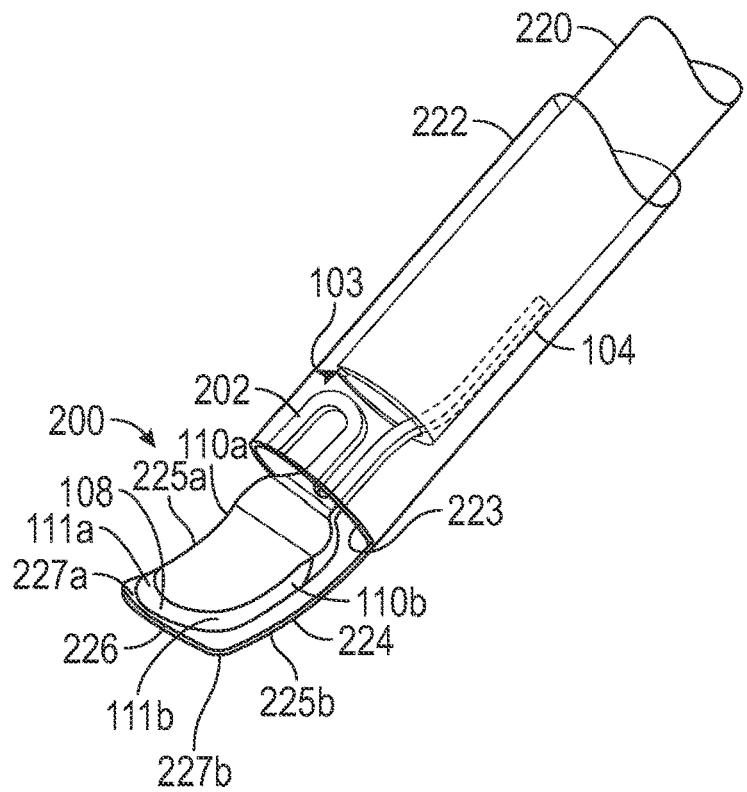
FIG. 2B illustrates a device with a curved lever being partially positioned within a shaft of a handle, in accordance with certain embodiments of the present disclosure.

In certain embodiments, device 100 is configured to be partially housed by an outer shaft (e.g., outer shaft 222) of the hand-piece, as shown in FIG. 2A. In the example of FIG. 1, the first lever 102 and second lever 104 are curved levers (e.g., levers with S-shaped curvatures). First lever 102 has a larger curvature than second lever 104. In certain embodiments, the distance between levers 102 and 104 may range from 0.2 to 0.5 millimeters (mm). This is because first lever 102 is configured to be fixedly coupled to the outer shaft 222 while second lever 104 is configured to be fixedly coupled to an inner shaft 220, which is positioned within the outer shaft 222 and has a smaller inner diameter than the outer shaft 222. In certain embodiments, the distance between lever 104 and the closest surface of the outer shaft 222 may range from 0.05 to 0.5 mm. Note that the shapes and lengths of first lever 102 and second lever 104 are merely exemplary (i.e., only one example embodiment). In certain other embodiments, one or both of the first lever 102 or the second lever 104 may have a U-shaped curvature, as shown in FIG. 2B. Also, in certain embodiments, both first lever 102 and second lever 104 may have the same curvature. In certain embodiments, lever 104 may also extend along the entire length of the outer shaft 222, as described below.

FIG. 2A illustrates device 100 partially positioned within an outer shaft 222 of a hand-piece. Outer shaft 222 includes a distal end 223 as well as a proximal end. The proximal end of outer shaft 222 is configured to be coupled to the hand-piece. Note that, herein, a distal end of a component refers to the end that is closer to a patient's body. On the other hand, the proximal end of the component refers to the end that is facing away from the patient's body.

A protective base 224 extends from outer shaft 222 to protect the retina from the sharp edges of device 100. In certain embodiments, protective base 224 and outer shaft 222 are manufactured as separate elements. In certain other embodiments, protective base 224 and outer shaft 222 are manufactured as a single element. As illustrated, protective base 224 is slightly curved. The curvature of protective base 224 reduces the likelihood of a tip 226 of protective base 224 making contact with or damaging the surface of the retina. As shown, protective base 224 includes sides 225a and 225b (referred to individually as "side 225a" and "side 225b," or collectively referred to as "sides 225") and corners 227a and 227b (referred to individually as "corner 227a" and "corner 227b," or collectively referred to as "corners 227").

The first lever 102 and the second lever 104 are at least partially housed by outer shaft 222 while blade 106 at least partially extends beyond the distal end 223 of outer shaft 222. The second lever 104 is fixedly coupled to an inner shaft 220. Inner shaft 220 includes a slit or an opening 103 through which the first lever 102 passes to be coupled to the inner surface of outer shaft 222. The opening 103 also allows the inner shaft 220 to move in a distal direction in relation to outer shaft 222 without making contact with the first lever 102.

Inner shaft 220 is configured to move longitudinally in distal and proximal directions in response to a push and pull force, respectively, applied thereto. In certain embodiments, outer shaft 222 and inner shaft 220 are coupled to a manual or hand-activated hand-piece, including a driver configured to linearly push and pull inner shaft 220 along its longitudinal axis. In certain other embodiments, outer shaft 222 and inner shaft 220 are coupled to an automated hand-piece that is connected to a console. In such embodiments, the automated hand-piece may include a mechanism configured to create longitudinal or linear motion to push and pull inner shaft 220 along its longitudinal axis. One of various hand-pieces and/or mechanisms may be used to actuate inner shaft 220 (e.g., move inner shaft 220 along its longitudinal axis), as one of ordinary skill in the art can appreciate.

FIG. 2A illustrates device 100 in an at-rest state, where the tip 108, sides 110, or corners 111 of blade 106 do not extend beyond the tip 226, sides 225, or corners 227 of protective base 224, respectively. However, longitudinally moving inner shaft 220 actuates device 100. More specifically, longitudinal movements of inner shaft 220 in distal and proximal directions move blade 106 distally, proximally, and sideways with respect to protective base 224. For example, pushing inner shaft 220 in a distal direction applies force on the second lever 104, which is then translated to blade 106 and moves blade 106 in a distal direction with respect to protective base 224. Moving blade 106 in a distal direction may cause the tip 108 of blade 106 to extend beyond the tip 226 of protective base 224 by at least some distance (e.g., around 0.01-0.1 millimeters (mm)).

However, because the first lever 102 is fixedly coupled to outer shaft 222, pushing the second lever 104 further in a distal direction does not cause blade 106 to move any further with respect to protective base 224 in a distal direction. In other words, the first lever 102 restricts the distal movement of blade 106 beyond a certain point by applying force to blade 106 in an opposite direction. As such, once the tip 108 of blade 106 extends beyond the tip 226 of protective base 224 by a certain distance, pushing the second lever 104 further in a distal direction causes blade 106 to move sideways towards side 225a of protective base 224. How far blade 106 is pushed towards side 225a depends on how far the second lever 104 is pushed in the distal direction. As further shown in FIG. 5, in one example, blade 106 is pushed far enough towards side 225a to cause the side 110a, or at least corner 111a, of blade 106 to extend beyond side 225a or corner 227a of protective base 224 by a certain distance (e.g., 0.01-0.1 mm). Accordingly, how far the second lever 104 is pushed in a distal direction in relation to outer shaft 222 can be configured based on how far the side 110a and/or corner 111a of blade 106 need to be extended beyond the side 225a or corner 227a for cutting purposes. Although in the example above blade 106 is pushed far enough towards side 225a to cause the side 110a, or at least the corner 111a, of blade 106 to extend beyond the side 225a or corner 227a of protective base 224, in another example, blade 106 may not be pushed that far.

After the second lever 104 travels the configured distance in the distal direction in relation to outer shaft 222, the second lever 104 is pulled in a proximal direction relative to the outer shaft 222. For example, inner shaft 220 may be pulled in a proximal direction, causing the second lever 104 to be pulled in that direction as well. The longitudinal movement of the second lever 104 in the proximal direction causes blade 106 to move back to its at-rest state, shown in FIG. 2A. However, pulling the second lever 104 in a proximal direction even further causes blade 106 to move sideways relative to and towards side 225b of protective base 224. For example, as further shown in FIG. 6, the second lever 104 may be pulled far enough to cause the side 110b, or at least the corner 111b, of blade 106 to extend beyond the side 225b or the corner 227b of protective base 224 by a certain distance (e.g., 0.5 mm). Accordingly, how far second lever 104 is pulled in a proximal direction in relation to outer shaft 222 can be configured based on how far the side 110b and/or corner 111b of blade 106 need to be extended beyond the side 225b or corner 227b of protective base 224 for cutting purposes. Although in the example above blade 106 is pushed far enough towards side 225a to cause the side 110a, or at least the corner 111a, to extend beyond the side 225b or corner 227b, in another example, blade 106 may not be pushed that far.

FIG. 2B illustrates device 200 partially positioned within outer shaft 222 of a hand-piece. Device 200 is different from device 100 because, device 200 includes a U-shaped or curved first lever, shown as first lever 202. The functionality of device 200, including how device 200 is actuated, is the same as described above in relation to device 100 of FIG. 2A.

Note that although in certain embodiments, such as in the embodiments shown in FIGS. 2A and 2B, the tip 226 of the protective base 224 extends beyond the tip 108 of the blade 106 when the blade is in its at rest position, in other embodiments, the tip 108 of the blade 106 extends beyond the tip 226 of the protective base 224 when the blade 106 is in its at rest position. In such embodiments, the tip 108 of the blade 106 always extends beyond the tip 226 of the protective base 224 by a certain distance (e.g., 0.01-0.1 mm) without the blade 106 being actuated (e.g., without any movements of the second lever 104). Further, in such embodiments, pushing the second lever 104 in a distal direction actuates blade 106 by moving it sideways towards side 225a. This causes the side 110a, or at least corner 111a, of blade 106 to extend beyond side 225a or corner 227a of protective base 224, as described above. Pulling second lever 104 in a proximal direction causes the blade to move sideways relative to and towards side 225b of protective base 224, which in turn causes the side 110b, or at least the corner 111b, of blade 106 to extend beyond the side 225b or the corner 227b of protective base 224.

Figure 3:
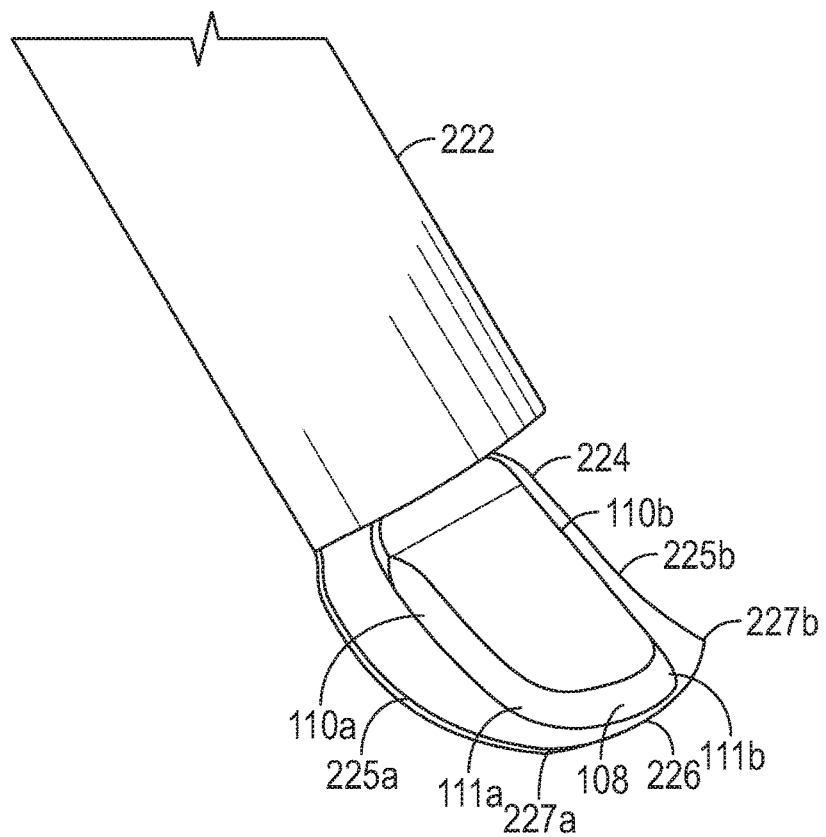
FIGS. 3-6 illustrates various positions of the device within a shaft of a hand-piece, in accordance with certain embodiments of the present disclosure.

FIG. 3 illustrates an example position of blade 106 with respect to protective base 224 when blade 106 is in an at-rest state (e.g., similar to FIGS. 2A-2B) while FIGS. 4-7 illustrate snapshots of the various positions of blade 106 with respect to protective base 224 when blade 106 is in an actuated or active state. As shown, in an at-rest state, the tip 226 of protective base 226 extends beyond the tip 108 of blade 106. As discussed, FIG. 3 illustrates one example of an at-rest state of blade 106. In other embodiments, the tip 108 of the blade 106 extends beyond the tip 226 of the protective base 224 when the blade 106 is in its at-rest position.

Figure 4:
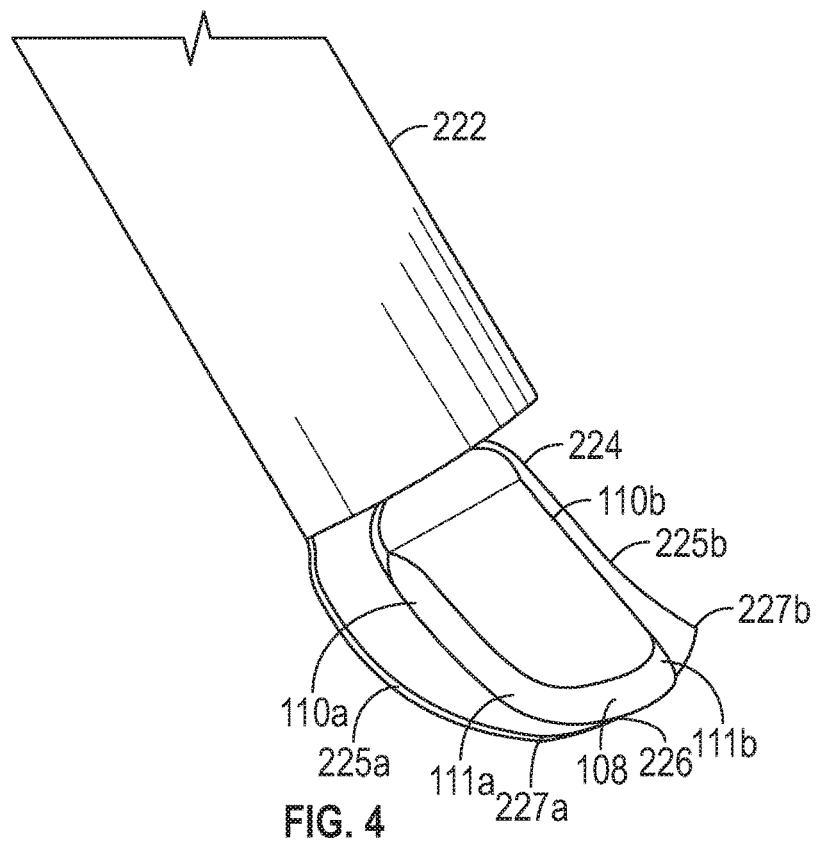

FIG. 4 illustrates an example position of blade 106, in which tip 108 of blade 106 extends in a distal direction beyond the tip 226 of the protective base 224. As described above, blade 106 is placed in this position when the second lever is pushed in a distal direction with respect to outer shaft 222. In one example, FIG. 4 illustrates a position of blade 106 where further movement of blade 106 in a distal direction is restricted by the first lever 102. As such, any further movement of the second lever in the distal direction causes blade 106 to move further sideways towards side 225a of protective base 224.

Note that the position of blade 106 in FIG. 4 corresponds to an at-rest state of the blade 106 in embodiments where the tip 108 of the blade 106 extends beyond the tip 226 of the protective base 224 in the at-rest position of blade 106. In other words, in such embodiments, the starting position of blade 106 corresponds to blade 106's position in FIG. 4. As such, any distal or proximal movement of lever 104 causes blade 106 to move sideways, as described above.

Figure 5:
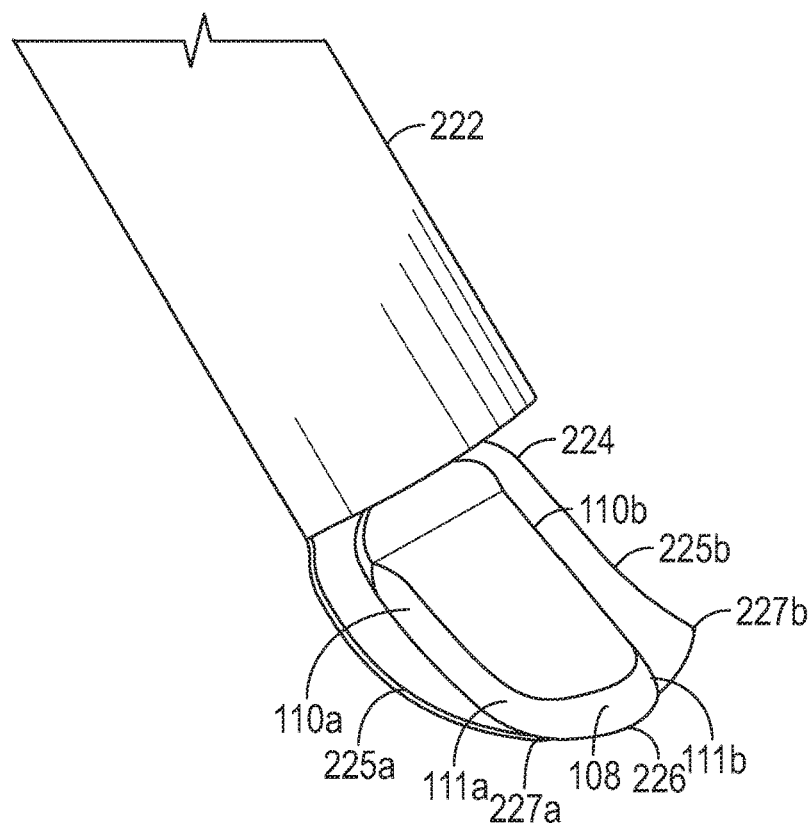

FIG. 5 illustrates an example position of blade 106, in which blade 106 has moved sideways towards side 225a of protective base 224 (e.g., as a result of a full longitudinal movement of the second lever 104 in a distal direction). As shown, in this example, the corner 111a of blade 106 extend(s) beyond the side 225a and corner 227a of protective base 224. As described above, in another example, blade 106 may not move far enough towards side 225a for the side 110a and/or corner 111a of blade 106 to extend beyond the side 225a and/or corner 227a of protective base 224. Once blade 106 has moved far enough towards side 225a of protective base 224, the second lever 104 is pulled in a proximal direction, thereby, causing blade 106 to move sideways towards side 225b of protective base 224.

Figure 6:
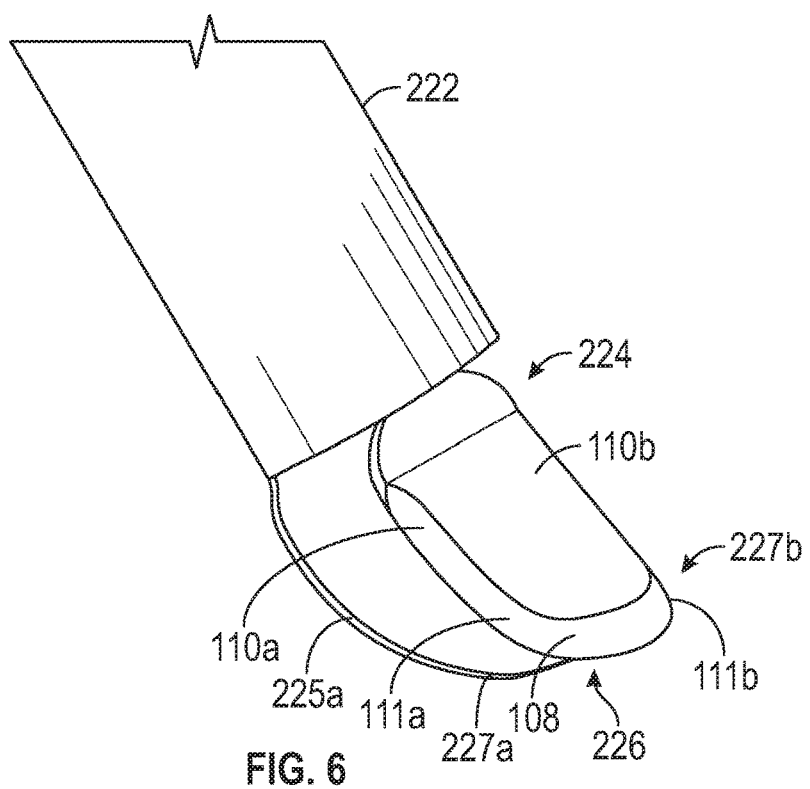

FIG. 6 illustrates an example position of blade 106, in which blade 106 has moved sideways towards side 225b of protective base 224 (e.g., as a result of a full longitudinal movement of the lever 104 in a proximal direction). As shown, in this example, the side 110b and corner 111b of blade 106 extend(s) beyond the side 225b and corner 227b of protective base 224. As described above, in another example, blade 106 may not move far enough towards side 225b for the side 110b and/or corner 111b of blade 106 to extend beyond the side 225b and/or corner 227b of protective base 224. Once the second lever moves far enough in the proximal direction, the hand-piece causes the second lever to move in the distal direction again. By longitudinally moving the second lever in the proximal and distal directions in an oscillating manner, blade 106 moves from side 225a to side 225b of protective base 224, thereby, cutting any connective tissue that it may come in contact with.

Figure 7:
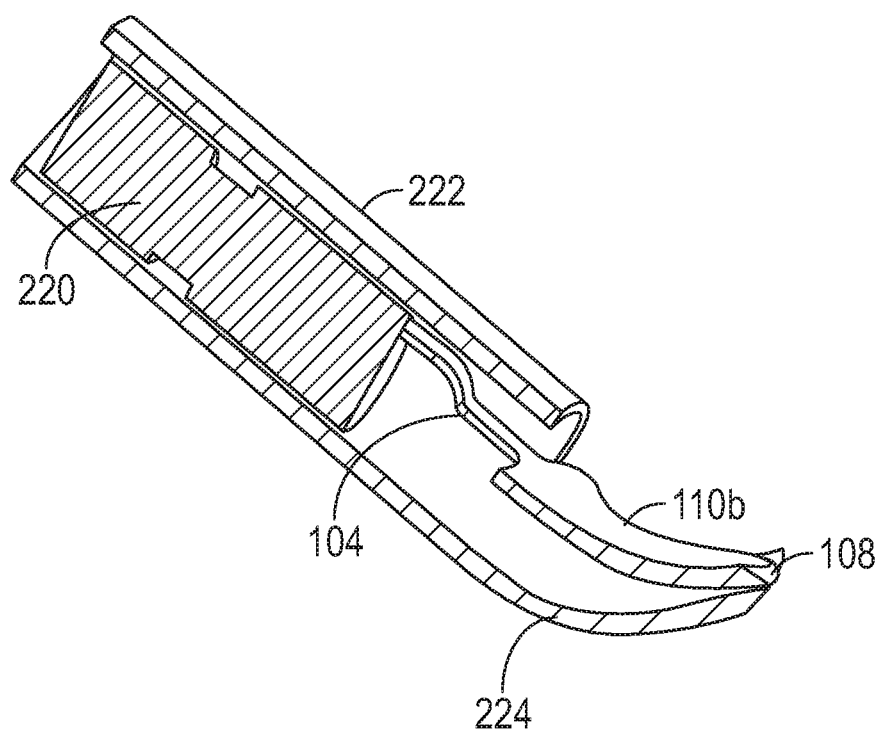
FIG. 7 illustrates a cross-sectional view of a device partially positioned within a shaft of a hand-piece, in accordance with certain embodiments of the present disclosure.

FIG. 7 illustrates a cross sectional view of device 100, outer shaft 222, and inner shaft 220.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A membrane delamination device for delaminating a membrane from a retina of an eye, comprising:
    a blade;
    a first lever coupled to the blade; and
    a second lever coupled to the blade, wherein:
        the first lever and the second lever are at least partially housed by a first shaft of a hand-piece;
        the first lever is fixedly coupled to the first shaft;
        the second lever is fixedly coupled to the hand-piece;
        the blade at least partially extends beyond a distal end of the first shaft;
        the membrane delamination device is configured to be actuated as a result of longitudinal movement of the second lever within and in relation to the first shaft; and
        the second lever moves longitudinally within and in relation to the first shaft due to an application of force to the second lever through the hand-piece.

2. The membrane delamination device of claim 1, wherein:
    longitudinal movement of the second lever in a distal direction causes the blade to move towards a first side of the first shaft;
    longitudinal movement of the second lever in a proximal direction causes the blade to move towards a second side of the first shaft.

3. The membrane delamination device of claim 1, wherein the first shaft is coupled to a protective base configured to be positioned between the blade and a surface of the retina to protect the retina from the blade.

4. The membrane delamination device of claim 3, wherein in an at-rest state of the membrane delamination device, a tip of the protective base extends beyond a tip of the blade.

5. The membrane delamination device of claim 4, wherein in an actuated state of the membrane delamination device, the tip of the blade extends beyond the tip of the protective base to cut connective tissues between the membrane and the retina.

6. The membrane delamination device of claim 5, wherein:

full longitudinal movement of the second lever in a distal direction causes a first corner of the blade to extend beyond at least one of a first side or a first corner of the protective base; and full longitudinal movement of the second lever in a proximal direction causes a second corner of the blade to extend beyond at least one of a second side or a second corner of the protective base.

7. The membrane delamination device of claim 3, wherein in an at-rest state of the membrane delamination device, a tip of the blade extends beyond a tip of the protective base.

8. The membrane delamination device of claim 7, wherein:

longitudinal movement of the second lever in a distal direction actuates the blade to move towards a first side of the first shaft;

longitudinal movement of the second lever in a proximal direction actuates the blade to move towards a second side of the first shaft.

9. The membrane delamination device of claim 1, wherein:

the second lever is fixedly coupled to a second shaft of the hand-piece;

the membrane delamination device is configured to be actuated as a result of longitudinal movement of the second shaft, which causes the longitudinal movement of the second lever within and in relation to the first shaft.

10. The membrane delamination device of claim 1, wherein a second shaft comprises a slit through which the first lever passes.

11. The membrane delamination device of claim 1, wherein:

the blade has a sharp tip, sharp corners, and sharp sides; and the blade is curved.

12. The membrane delamination device of claim 1, wherein the first lever is curved.

13. A hand-piece for delaminating a membrane from a retina of an eye, comprising:

a first shaft;

a membrane delamination device, comprising: a blade;

a first lever coupled to the blade; and a second lever coupled to the blade, wherein:

the first lever and the second lever are at least partially housed by the first shaft; and the first lever is fixedly coupled to the first shaft;

the second lever is fixedly coupled to the hand-piece;

the blade at least partially extends beyond a distal end of the first shaft;

the hand-piece is configured to actuate the membrane delamination device by longitudinally moving the second lever within and in relation to the first shaft.

14. The hand-piece of claim 13, wherein:

longitudinal movement of the second lever in a distal direction causes the blade to move towards a first side of the first shaft; and longitudinal movement of the second lever in a proximal direction causes the blade to move towards a second side of the first shaft.

15. The hand-piece of claim 13, further comprising:

a protective base coupled to the first shaft, the protective base configured to be positioned between the blade and a surface of the retina to protect the retina from the blade.

16. The hand-piece of claim 15, wherein:

in an at-rest state of the membrane delamination device, a distal end of the protective base extends beyond a distal end of the blade; and in an actuated state of the membrane delamination device, the blade extends beyond a tip of the protective base to cut connective tissues between the membrane and the retina.

17. The hand-piece of claim 16, wherein:

full longitudinal movement of the second lever in a distal direction causes a first corner of the blade to extend beyond at least one of a first side or a first corner of the protective base; and full longitudinal movement of the second lever in a proximal direction causes a second corner of the blade to extend beyond at least one of a second side or a second corner of the protective base.

18. The hand-piece of claim 15, wherein in an at-rest state of the membrane delamination device, a tip of the blade extends beyond a tip of the protective base.

19. The hand-piece of claim 18, wherein:

longitudinal movement of the second lever in a distal direction actuates the blade to move towards a first side of the first shaft;

longitudinal movement of the second lever in a proximal direction actuates the blade to move towards a second side of the first shaft.

20. The hand-piece of claim 13, further comprising:

a second shaft positioned within the first shaft, wherein:

the second lever is fixedly coupled to the second shaft of the hand-piece; and the hand-piece being configured to actuate the membrane delamination device further comprises the hand-piece being configured to actuate the membrane delamination device by longitudinally moving the second shaft within and in relation to the first shaft, which causes longitudinal movement of the second lever within and in relation to the first shaft.

* * * * *